US007087610B2

(12) United States Patent
Wang et al.

(10) Patent No.: US 7,087,610 B2
(45) Date of Patent: Aug. 8, 2006

(54) BENZOTHIAZOLE ANTIVIRAL AGENTS

(75) Inventors: Tao Wang, Middletown, CT (US); John F. Kadow, Wallingford, CT (US); Nicholas A. Meanwell, East Hampton, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/125,066

(22) Filed: May 9, 2005

(65) Prior Publication Data

US 2005/0272734 A1  Dec. 8, 2005

Related U.S. Application Data

(60) Provisional application No. 60/576,850, filed on Jun. 3, 2004.

(51) Int. Cl.
*A61K 31/496* (2006.01)
*C07D 417/06* (2006.01)
*C07D 417/14* (2006.01)

(52) U.S. Cl. .......................... 514/254.02; 514/525.19; 514/253.1; 514/248; 514/252.17; 514/253.06; 514/321; 544/235; 544/284; 544/295; 544/363; 544/364; 544/368; 546/198

(58) Field of Classification Search ................ 544/368; 514/254.02
See application file for complete search history.

(56) References Cited

U.S. PATENT DOCUMENTS

| 6,469,006 B1 | 10/2002 | Blair et al. |
| 6,476,034 B1 | 11/2002 | Wang et al. |
| 6,573,262 B1 | 6/2003 | Wallace et al. |
| 6,632,819 B1 | 10/2003 | Wang et al. |
| 2004/0063744 A1 | 4/2004 | Wang et al. |

FOREIGN PATENT DOCUMENTS

WO  WO 03/092695 A1  11/2003

OTHER PUBLICATIONS

Vippagunta et al Advanced Drug Delivery Reviews, vol. 48, pp. 3-26 (2001).*
Juliang Zhu, et al, "A One-Pot Synthesis of Nitrogen-Containing Heteroaryl α-Keto Amides from Heteroaryl Halides," Tetrahedron Letters, 46(20), pp. 3587-3589, 2005.
U.S. Appl. No. 10/214,982, filed Aug. 7, 2002, Tao Wang et al.

* cited by examiner

*Primary Examiner*—Emily Bernhardt
(74) *Attorney, Agent, or Firm*—James Epperson

(57) ABSTRACT

The invention encompasses a series of benzothiazole compounds which inhibit HIV entry and are useful for treating HIV infection and AIDS. The invention also encompasses pharmaceutical compositions and methods for using these compounds.

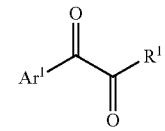

I

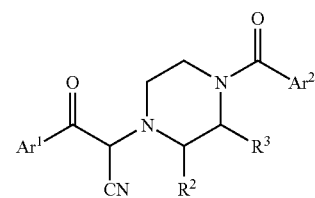

IIa

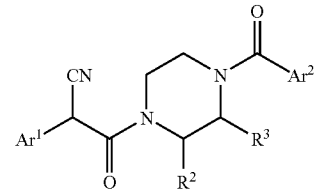

IIb

18 Claims, No Drawings

BENZOTHIAZOLE ANTIVIRAL AGENTS

CROSS REFERENCE TO RELATED APPLICATIONS

This application claims the benefit of U.S. provisional application U.S. Ser. No. 60/576,850 filed Jun. 3, 2004.

BACKGROUND OF THE INVENTION

HIV-1 (human immunodeficiency virus-1) infection remains a major medical problem, with an estimated 42 million people infected worldwide at the end of 2002. The number of cases of HIV and AIDS (acquired immunodeficiency syndrome) has risen rapidly. In 2002, ~5.0 million new infections were reported, and 3.1 million people died from AIDS. Currently available drugs for the treatment of HIV include nine nucleoside reverse transcriptase (RT) inhibitors or approved single pill combinations(zidovudine or AZT (or Retrovir®), didanosine (or Videx®), stavudine (or Zerit®), lamivudine (or 3TC or Epivir®), zalcitabine (or DDC or Hivid®), abacavir succinate (or Ziagen®), Tenofovir disoproxil fumarate salt (or Viread®), Combivir® (contains -3TC plus AZT), Trizivir® (contains abacavir, lamivudine, and zidovudine); three non-nucleoside reverse transcriptase inhibitors: nevirapine (or Viramune®), delavirdine (or Rescriptor®) and efavirenz (or Sustiva®), and seven peptidomimetic protease inhibitors or approved formulations: saquinavir, indinavir, ritonavir, nelfinavir, amprenavir, lopinavir, and Kaletra® (lopinavir and Ritonavir). Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present. Therefore, novel anti-HIV agents exhibiting distinct resistance patterns, and favorable pharmacokinetic as well as safety profiles are needed to provide more treatment options.

Currently marketed HIV-1 drugs are dominated by either nucleoside reverse transcriptase inhibitors or peptidomimetic protease inhibitors. Non-nucleoside reverse transcriptase inhibitors (NNRTIs) have recently gained an increasingly important role in the therapy of HIV infections. At least 30 different classes of NNRTI have been described in the literature and several NNRTIs have been evaluated in clinical trials. Dipyridodiazepinone (nevirapine), benzoxazinone (efavirenz) and bis(heteroaryl) piperazine derivatives (delavirdine) have been approved for clinical use. However, the major drawback to the development and application of NNRTIs is the propensity for rapid emergence of drug resistant strains, both in tissue cell culture and in treated individuals, particularly those subject to monotherapy. As a consequence, there is considerable interest in the identification of NNRTIs less prone to the development of resistance.

The compounds of this invention inhibit HIV entry by attaching to the exterior viral envelop protein gp120 and interrupting the viral entry process, possibly by interfering with recognition of the cellular receptor CD4. Compounds in this class have been reported to have antiviral activity against a variety of laboratory and clinical strains of HIV-1 and are effective in treating HIV infection (see Hanna et al., Abstract 141 presented at the 11th Conference on Retroviruses and Opportunistic Infections, San Francisco, Calif., Feb. 8–11, 2004; Lin et al., Poster 534 presented at the 11th Conference on Retroviruses and Opportunistic Infections, San Francisco, Calif., Feb. 8–11, 2004; Hanna et al., Poster 535 presented at the 11th Conference on Retroviruses and Opportunistic Infections, San Francisco, Calif., Feb. 8–11, 2004).

N-(3-aryl-3-oxo)acetyl piperidines have been disclosed. See Blair et al., U.S. Pat. No. 6,469,006; Wang et al., U.S. Pat. No. 6,476,034; Wang et al., U.S. Pat. No. 6,632,819; Wallace et al., U.S. Pat. No. 6,573,262 (continuation-in-part application of U.S. Ser. No. 09/888,686, filed Jun. 25, 2001); Wang et al., U.S. patent application Ser. No. 10/214,982 filed Aug. 7, 2002 (continuation-in-part application of U.S. Ser. No. 10/038,306 filed Jan. 2, 2002); Wang et al., patent application WO 03/092695, published Nov. 13, 2003; Wang et al., U.S. patent application US 20040063744, published Apr. 1, 2004. Nothing in these references teaches or suggests the novel compounds of this invention or their use to inhibit HIV infection.

DESCRIPTION OF THE INVENTION

The invention encompasses compounds of Formula I, IIa, and IIb including pharmaceutically acceptable salts and solvates, their pharmaceutical compositions, and their use in treating those infected with HIV.

One aspect of the invention are compounds of Formula I

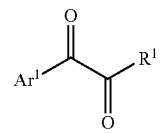

wherein:

$R^1$ is

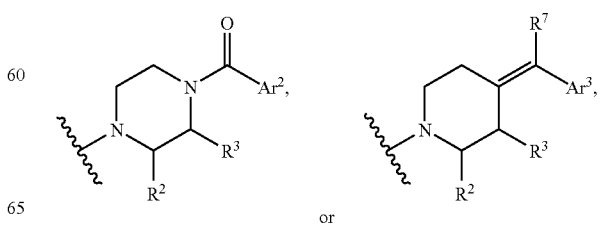

or

-continued

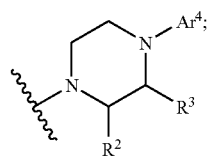

R² and R³ are independently hydrogen or $C_{1-6}$alkyl;

R⁴ and R⁵ are independently hydrogen, halo, cyano, $C_{1-6}$alkoxy, $CO_2R^2$, $CON(R^2)(R^2)$, or Ar⁵;

R⁶ is hydrogen, amino, $C_{1-6}$alkylamino, $C_{1-6}$dialkylamino, or pyrrolyl;

R⁷ is cyano or is an aryl group selected from the group consisting of phenyl, oxadiazolyl, and pyrazolyl where the aryl group is substituted with 0–2 substituents selected from halo and $C_{1-6}$alkyl;

Ar¹ is

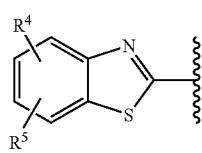 or 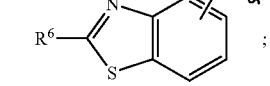 ;

Ar² is phenyl, furanyl, thienyl, or pyrrolyl and is substituted with 0–2 substituents selected from the group consisting of $C_{1-6}$alkoxy, halo, trifluoromethyl, cyano, amino, and hydroxy;

Ar³ is phenyl, furanyl, or pyridyl and is substituted with 0–2 substituents selected from the group consisting of $C_{1-6}$alkoxy, halo, trifluoromethyl, cyano, amino, and hydroxy;

Ar⁴ is

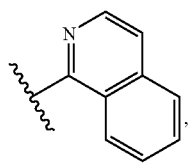 , 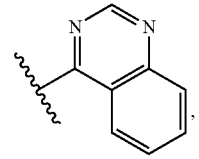 , or

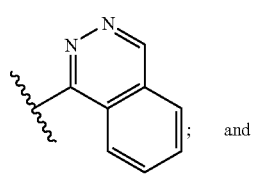 ; and

Ar⁵ is pyridinyl, pyrimidinyl, pyrazolyl, triazolyl, or tetrazolyl, and is substituted with 0–1 $C_{1-6}$alkyl;

or a pharmaceutically acceptable salt or solvate thereof.

Another aspect of the invention are compounds of Formula IIa or IIb.

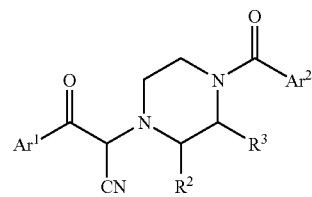

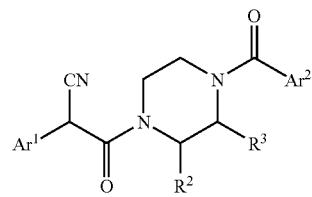

Another aspect of the invention are compounds of Formula I, IIa, or IIb where Ar¹ is

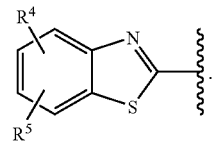

Another aspect of the invention are compounds of Formula I, IIa, or IIb where Ar¹ is

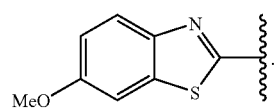

Another aspect of the invention are compounds of Formula I, IIa, or IIb where Ar¹

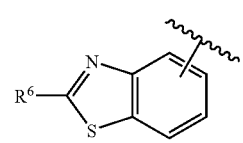

Another aspect of the invention are compounds of Formula I, IIa, or IIb where R⁶ is hydrogen, amino, or pyrrolyl.

Another aspect of the invention are compounds of Formula I, IIa, or IIb where R² and R³ are hydrogen.

Another aspect of the invention are compounds of Formula I, IIa, or IIb where R² is hydrogen and R³ is methyl.

Another aspect of the invention are compounds of Formula I, IIa, or IIb where R² is methyl and R³ is hydrogen.

Another aspect of the invention are compounds of Formula I, IIa, or IIb where R⁴ is methoxy or triazolyl where the triazolyl moiety is substituted with 0–1 $C_{1-6}$alkyl.

Another aspect of the invention are compounds of Formula I, IIa, or IIb where Ar² is phenyl substituted with 0–2 substituents selected from the group consisting of $C_{1-6}$alkoxy, halo, trifluoromethyl, cyano, amino, and hydroxy.

Another aspect of the invention are compounds of Formula I, IIa, or IIb where $Ar^2$ is phenyl.

Some compounds of the invention are
1-(2-benzothiazolylcyanoacetyl)-4-benzoyl-2-methyl-piperazine;
(2R)-1-[2-(2-benzothiazolyl)-1,2-dioxoethyl]-4-benzoyl-2-methyl-piperazine;
(2R)-4-benzoyl-1-[2-(6-methoxy-2-benzothiazolyl)-1,2-dioxoethyl]-2-methyl-piperazine;
(2R)-1-[2-(5-benzothiazolyl)-1,2-dioxoethyl]-4-benzoyl-2-methyl-piperazine;
(2R)-4-benzoyl-1-[1,2-dioxo-2-[2-(1H-pyrrol-1-yl)-5-benzothiazolyl]ethyl]-2methyl-piperazine and
(2R)-1-[2-(2-amino-5-benzothiazolyl)-1,2-dioxoethyl]-4-benzoyl-2-methyl-piperazine;

and pharmaceutically acceptable salts and solvates thereof.

"Alkyl," "alkoxy" and related terms with an alkyl moiety include straight and branched configurations. "Aryl" includes carbocyclic and heterocyclic aromatic ring systems.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, lysine, arginine, N-methylglucamine, and zinc.

The invention also includes all solvated forms of the compounds, particularly hydrates. Solvates do not contribute significantly to the physiological activity or toxicity of the compounds and as such function as pharmacological equivalents. Solvates may form in stoichiometric amounts or may form from adventitious solvent or a combination of both. One type of solvate is hydrate, and some hydrated forms include monohydrate, hemihydrate, and dihydrate.

Synthetic Methods

The compounds of this invention can be made according to the schemes provided and other reactions known in the art. Schemes 1–3 illustrate procedures for making and modifying some compounds of the invention. Other related syntheses are known in the art. Further synthetic procedures are described in the specific embodiments section.

Compounds where $R^1$ is

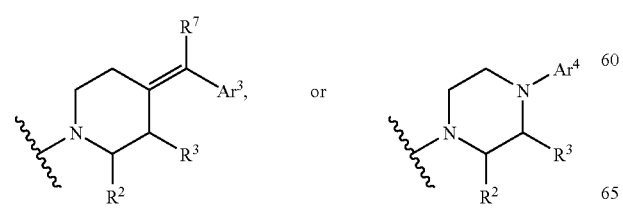

can be made using methods described in Wang et al., U.S. patent application US 20040063744; U.S. patent application Ser. No. 10/762108, filed Jan. 21, 2004; and U.S. patent application Ser. No. 60/541970, filed Feb. 5, 2004. These references are incorporated by reference.

Scheme 1.

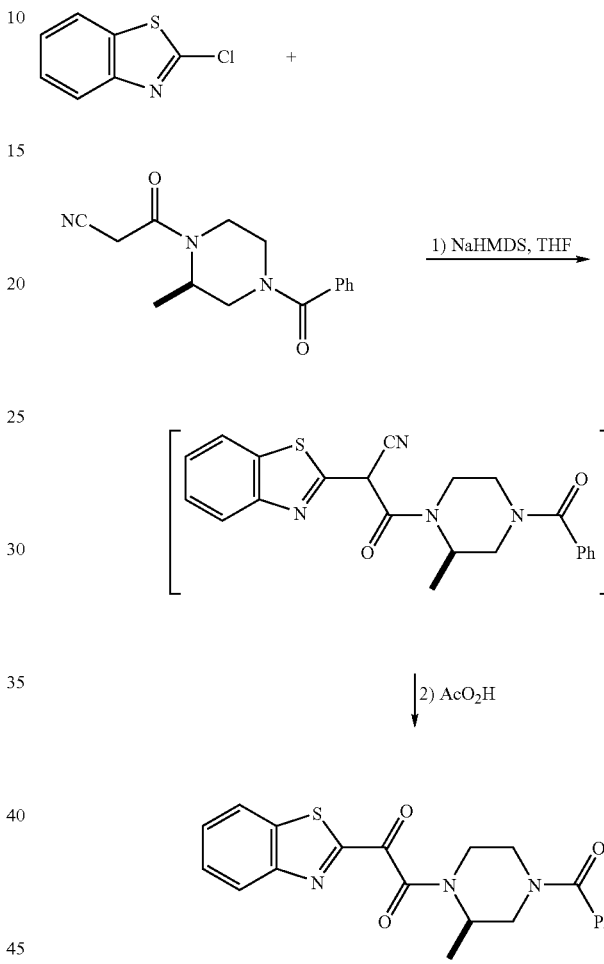

Scheme 2.

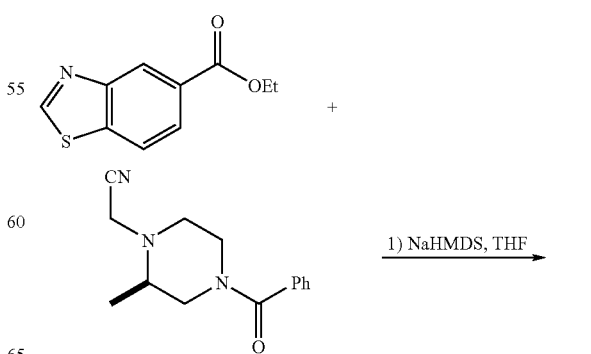

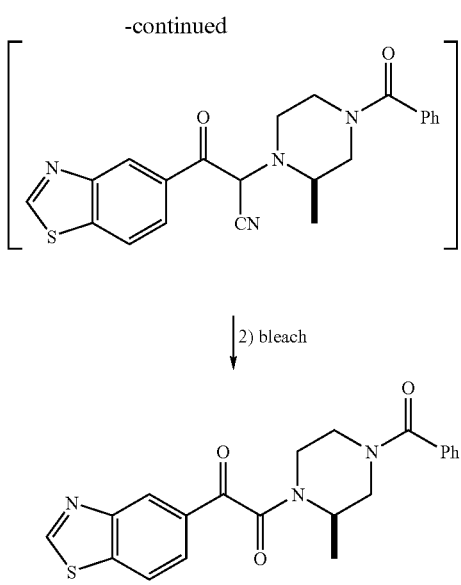

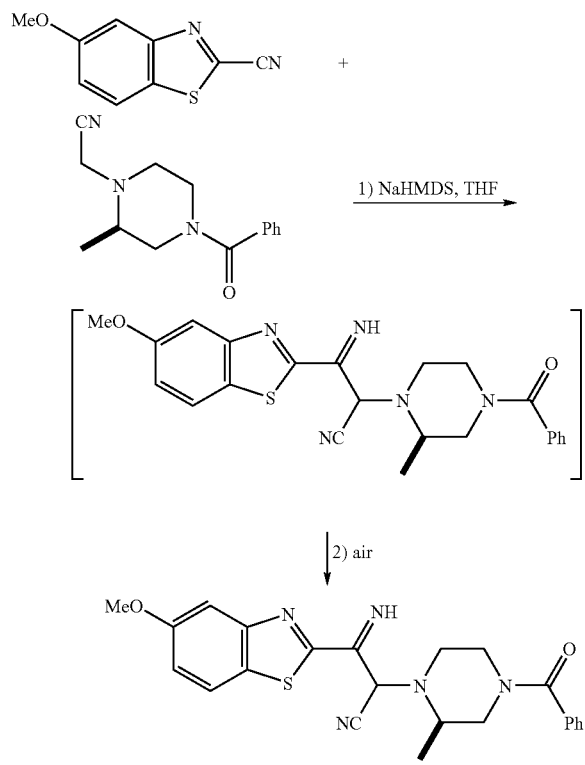

Biological Methods

Cells: (virus production) human embryonic kidney cell line, 293, was propagated in Dulbecco's Modified Eagle Medium (Invitrogen, Carlsbad, Calif.) containing 10% fetal Bovine serum (FBS, Sigma, St. Louis, Mo.); (virus infection) human epithelial cell line, HeLa, expressing the HIV-1 receptor CD4 was propagated in Dulbecco's Modified Eagle Medium (Invitrogen, Carlsbad, Calif.) containing 10% fetal Bovine serum (FBS, Sigma, St. Louis, Mo.) and supplemented with 0.2 mg/mL Geneticin (Invitrogen, Carlsbad, Calif.).

Virus: single-round infectious reporter virus was produced by co-transfecting human embryonic kidney 293 cells with an HIV-1 envelope DNA expression vector and a proviral cDNA containing an envelope deletion mutation and the luciferase reporter gene inserted in place of HIV-1 nef sequences. Transfections were performed using lipofectAMINE PLUS reagent as described by the manufacturer (Invitrogen, Carlsbad, Calif.).

Experiment: HeLa CD4 cells were plated in 96 well plates at a cell density of 1×104 cells per well in 100 µl Dulbecco's Modified Eagle Medium containing 10 % fetal Bovine serum and incubated overnight. Compound was added in a 2 µl dimethylsulfoxide solution, so that the final assay concentration would be $\leq 10$ µM. Single-round infectious reporter virus (100 µL) in Dulbecco's Modified Eagle Medium was then added to the plated cells and compound at an approximate multiplicity of infection (MOI) of 0.01, resulting in a final volume of 200 µl per well. Virally-infected cells were incubated at 37 degrees Celsius, in a CO2 incubator, and harvested 72 h after infection. Viral infection was monitored by measuring luciferase expression from viral DNA in the infected cells using a luciferase reporter gene assay kit, as described by the manufacturer (Roche Molecular Biochemicals, Indianapolis, Ind.). Infected cell supernatants were removed and 50 µl of lysis buffer was added per well. After 15 minutes, 50 µl of freshly-reconstituted luciferase assay reagent was added per well. Luciferase activity was then quantified by measuring luminescence using a Wallac microbeta luminescence reader.

The percent inhibition for each compound was calculated by quantifying the level of luciferase expression in cells infected in the presence of each compound as a percentage of that observed for cells infected in the absence of compound and subtracting such a determined value from 100. The effective concentration for fifty percent inhibition ($EC_{50}$) was calculated with Microsoft Excel Xlfit curve fitting software. For each compound, curves were generated from percent inhibition calculated at 10 different concentrations by using a four parameter logistic model (model 205). The $EC_{50}$ data for the compounds is shown in Table 1.

TABLE 1

| Example | $EC_{50}$ |
|---------|-----------|
| 1 | A |
| 2 | A |
| 4 | A |
| 5 | A |
| 6 | A |
| 7 | A |
| 8 | A |

$EC_{50}$ <1 µM = A;
1–5 µM = B;
>5 µM = C;
>0.5 µM = D.

Pharmaceutical Composition and Methods of Use

The compounds of this invention inhibit HIV entry by attaching to the exterior viral envelop protein gp120 and interrupting the viral entry process, possibly by interfering with recognition of the cellular receptor CD4. Compounds in this class have been reported to have antiviral activity against a variety of laboratory and clinical strains of HIV-1 and are effective in treating HIV infection (see Hanna et al., Abstract 141 presented at the 11th Conference on Retroviruses and Opportunistic Infections, San Francisco, Calfi., Feb. 8–11, 2004; Lin et al., Poster 534 presented at the 11th Conference on Retroviruses and Opportunistic Infections, San Francisco, Calif., Feb. 8–11, 2004; Hanna et al., Poster 535 presented at the 11th Conference on Retroviruses and Opportunistic Infections, San Francisco, Calif., Feb. 8–11, 2004).

Accordingly, another aspect of the invention is a method for treating HIV infection in a human patient comprising administering a therapeutically effective amount of a compound of Formula I, IIa, or IIb, or a pharmaceutically acceptable salt or solvate thereof, with a pharmaceutically acceptable carrier.

Another aspect of the invention is a method for treating HIV infection in a human patient comprising administering a therapeutically effective amount of a compound of Formula I, IIa, or IIb, or a pharmaceutically acceptable salt or solvate thereof, with a therapeutically effective amount of at least one other agent used for treatment of AIDS or HIV infection. Some suitable agents are nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a composition for treating HIV infection in a human patient comprising administering a therapeutically effective amount of a compound of Formula I, IIa, or IIb, or a pharmaceutically acceptable salt or solvate thereof, with a pharmaceutically acceptable carrier.

"Combination," "coadministration," "concurrent," and similar terms referring to the administration of compounds of Formula I, IIa, and IIb with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I, IIa, or IIb, or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25–1000 mg/unit.

Liquid compositions are usually in dosage unit ranges. Generally, the liquid composition will be in a unit dosage range of 1–100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1–100 mg/mL.

The invention encompasses all conventional modes of administration; oral and parenteral methods are preferred. Generally, the dosing regimen will be similar to other antiretroviral agents used clinically. Typically, the daily dose will be 1–100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compounds of this invention will generally be given in a daily dose of 1–100 mg/kg body weight daily in conjunction with other agents. The other agents generally will be given in the amounts used therapeutically. The specific dosing regime, however, will be determined by a physician using sound medical judgement.

Table 2 lists some agents useful in treating AIDS and HIV infection which are suitable for this invention.

TABLE 2

| | Antivirals | |
|---|---|---|
| DRUG NAME | MANUFACTURER | INDICATION |
| 097 (non-nucleoside reverse transcriptase inhibitor) | Hoechst/Bayer | HIV infection, AIDS, ARC |

TABLE 2-continued

Antivirals

| DRUG NAME | MANUFACTURER | INDICATION |
|---|---|---|
| Amprenavir 141 W94 GW 141 (protease inhibitor) | Glaxo Wellcome | HIV infection, AIDS, ARC |
| Abacavir (1592U89) GW 1592 (RT inhibitor) | Glaxo Wellcome | HIV infection, AIDS, ARC |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection, ARC, |
| AL-721 | Ethigen (Los Angeles, CA) | PGL HIV positive, AIDS |
| Alpha Interferon HIV in combination w/Retrovir | Glaxo Wellcome | Kaposi's sarcoma |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-232623 (CGP-73547) (protease inhibitor) | Bristol-Myers Squibb/ Novartis | HIV infection, AIDS, ARC |
| BMS-234475 (CGP-61755) (protease inhibitor) | Bristol-Myers Squibb/ Novartis | HIV infection, AIDS, ARC |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral, CMV retinitis |
| Delaviridine (RT inhibitor) | Pharmacia-Upjohn | HIV infection, AIDS, ARC |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combinationwith AZT/d4T |
| DMP-450 (protease inhibitor) | AVID (Camden, NJ) | HIV infection, AIDS, ARC |
| Efavirenz (DMP 266) (−)6-Chloro-4-(S)-cyclopropylethynyl-4(S)-trifluoro-methyl-1,4-dihydro-2H-3,1-benzoxazin-2-one, STOCRINE (non-nucleoside RT inhibitor) | DuPont Merck | HIV infection, AIDS, ARC |
| EL10 | Elan Corp, PLC (Gainesville, GA) | HIV infection |
| Famciclovir | Smith Kline | herpes zoster, herpes simplex |
| FTC (reverse transcriptase | Emory University | HIV infection, AIDS, ARC |

TABLE 2-continued

Antivirals

| DRUG NAME | MANUFACTURER | INDICATION |
|---|---|---|
| inhibitor) | | |
| GS 840 (reverse transcriptase inhibitor) | Gilead | HIV infection, AIDS, ARC |
| HBY097 (non-nucleoside reverse transcriptaseinhibitor) | Hoechst Marion Roussel | HIV infection, AIDS, ARC |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-associated diseases |
| Lamivudine, 3TC (reverse transcriptase inhibitor) | Glaxo Wellcome | HIV infection, AIDS, ARC, also with AZT |
| Lobucavir | Bristol-Myers Squibb | CMV infection |
| Nelfinavir (protease inhibitor) | Agouron Pharmaceuticals | HIV infection, AIDS, ARC |
| Nevirapine (RT inhibitor) | Boeheringer Ingleheim | HIV infection, AIDS, ARC |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 (protease inhibitor) | Pharmacia Upjohn | HIV infection, AIDS, ARC |
| Probucol | Vyrex | HIV infection, AIDS |
| RBC-CD4 | Sheffield Med. Tech (Houston, TX) | HIV infection, AIDS, ARC |
| Ritonavir (protease inhibitor) | Abbott | HIV infection, AIDS, ARC |
| Saquinavir (protease inhibitor) | Hoffmann-LaRoche | HIV infection, AIDS, ARC |
| Stavudine; d4T Didehydrodeoxy-thymidine | Bristol-Myers Squibb | HIV infection, AIDS, ARC |
| Valaciclovir | Glaxo Wellcome | Genital HSV & CMVinfections |
| Virazole Ribavirin | Viratek/ICN (Costa Mesa, CA) | asymptomatic HIV-positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (Viread ®) (reverse transcriptase inhibitor) | Gilead | HIV infection, AIDS |
| Combivir ® (reverse transcriptase inhibitor) | GSK | HIV infection, AIDS |
| abacavir succinate (or Ziagen ®) (reverse transcriptase inhibitor) | GSK | HIV infection, AIDS |
| Reyataz ® (atazanavir) | Bristol-Myers Squibb | HIV infection, AIDS |
| Fuzeon (Enfuvirtide, T-20) | Roche/Trimeris | HIV infection, AIDS, viral fusion inhibitor |
| Trizivir ® | | HIV infection, AIDS |

TABLE 2-continued

Antivirals

| DRUG NAME | MANUFACTURER | INDICATION |
|---|---|---|
| Kaletra ® | Abbott | HIV infection, AIDS, ARC |

Immunomodulators

| DRUG NAME | MANUFACTURER | INDICATION |
|---|---|---|
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldesleukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma AIDS, in combination w/AZT |
| Granulocyte Colony Stimulating Factor | Amgen | |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma, AIDS, in combination w/AZT ARC |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |

Anti-infectives

| DRUG NAME | MANUFACTURER | INDICATION |
|---|---|---|
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

DESCRIPTION OF SPECIFIC EMBODIMENTS

All Liquid Chromatography (LC) data were recorded on a Shimadzu LC-10AS liquid chromatograph using a SPD-10AV UV-Vis detector with Mass Spectrometry (MS) data determined using a Micromass Platform for LC in electrospray mode.

LC/MS Method (i.e., compound identification). Column A: YMC ODS-A S7 3.0×50 mm column; Column B: PHX-LUNA C18 4.6×30 mm Column; Column C: XTERRA ms C18 4.6×30 mm column; Column D: YMC ODS-A C18 4.6×30 mm column; Column E: YMC ODS-A C18 4.6×33 mm column; Column F: YMC C18 S5 4.6×50 mm column; Column G: XTERRA C18 S7 3.0×50 mm column; Column H: YMC C18 S5 4.6×33 mm column; Column I: YMC ODS-A C18 S7 3.0×50 mm column; Column J: XTERRA C-18 S5 4.6×50 mm column; Column K: YMC ODS-A C18 4.6×33 mm column; Column L: YMC ODS-A C18 S3 4.6×33 mm column; Gradient: 100% Solvent A/0% Solvent B to 0% Solvent A/100% Solvent B; Gradient time: 2 minutes; Hold time: 1 minute; Flow rate: 5 ml/min; Detector Wavelength: 220 nm; Solvent A: 10% MeOH/90% H2O/0.1% Trifluoroacetic Acid; Solvent B: 10% H2O/90% MeOH/0.1% Trifluoroacetic Acid.

Compounds purified by preparative HPLC were diluted in methanol (1.2 ml) and purified using the following methods on a Shimadzu LC-10A automated preparative HPLC system.

Preparative HPLC Method (i.e., compound purification). Purification Method: Initial gradient (40% B, 60% A) ramp to final gradient (100% B, 0% A) over 20 minutes, hold for 3 minutes (100% B, 0% A); Solvent A: 10% MeOH/90% H$_2$O/0.1% Trifluoroacetic Acid; Solvent B: 10% H$_2$O/90% MeOH/0.1% Trifluoroacetic Acid; Column: YMC C18 S5 20×100 mm column; Detector Wavelength: 220 nm.

Intermediate 1

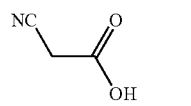

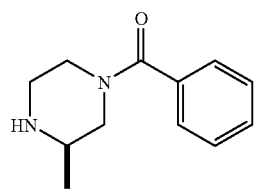

Preparation of (R)-N-benzoyl-N'-(2-cyano-acetyl)-2-methylpiperazine. DCC (2.43 g) and triethylamine (5 ml) were added into a solution of cyanoacetic acid (1.00 g) and (R)-N-benzoyl-3-methylpiperazine (2.84 g) in THF (50 ml). After reaction stirred at room temperature for 12 hours, solvents were removed under vacuum to give a residue which was purified by silica gel column chromatography to afford 3 g of (R)-N-benzoyl-3-methyl-N'-(2-cyano-acetyl) piperazine. MS m/z: (M+H)$^+$ calcd for C$_{15}$H$_{18}$N$_3$O$_2$ 272.14, found 272.17. HPLC retention time: 0.93 minutes (column H).

Intermediate 2

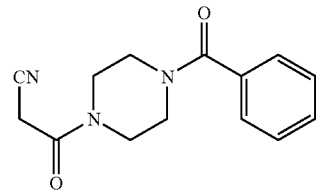

Preparation of N-benzoyl-N'-(2-cyano-acetyl)piperazine. N-benzoyl-N'-(2-cyano-acetyl)piperazine was prepared by the same method for of (R)-N-benzoyl-3-methyl-N'-(2-cyano-acetyl)piperazine. MS m/z: (M+H)$^+$ calcd for C$_{14}$H$_{16}$N$_3$O$_2$ 258.12, found 258.15. HPLC retention time: 0.83 minutes (column H).

Intermediate 3

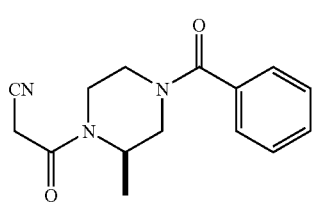

N-benzyl-N'-cyanomethylpiperazine. An excess of chloroacetonitrile (7 ml) was added in to a solution of benzylpiperazine (2 g, 10.5 mmol) in THF (100 ml) and Et$_3$N (10 ml). The reaction was stirred for 10 hours before quenched with saturated aqueous NaHCO$_3$ (100 ml). The aqueous phase was extracted with EtOAc (3×100 ml). The combined organic layer was dried over MgSO$_4$ and concentrated to a residue, which was used in the further reactions without any purification.

The following intermediates were prepared using the methods described above.

| Structure | MS (M + H)$^+$ Observ. And Calcd. | MS(M + H)$^+$ Retention Time |
|---|---|---|
| 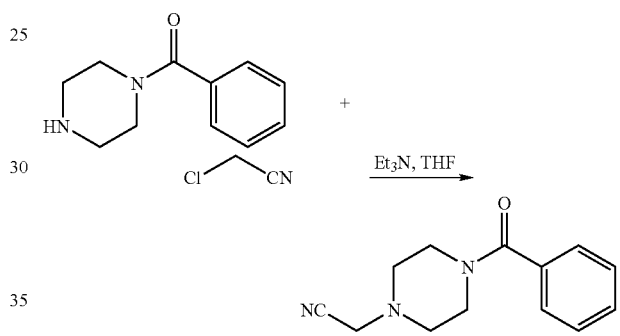 | 230.13 | 230.02 0.84 min (column I) |
| | 244.14 | 244.09 0.96 min (column I) |

| (M + H)+ Structure | MS (M + H)+ Observ. And Calcd. | MS(M + H)+ Retention Time |
|---|---|---|
| NC-CH2-N(piperazine)N-C(=O)-phenyl | 244.14 | 244.09 0.95 min (column I) |

EXAMPLE 1

(R)-N-(benzoyl)-3-methyl-N'-[(benzothiazol-2-yl)-2-cyanoacetyl]-piperazine. NaHMDS (1.48 ml, 1M in THF) was added into a solution of (R)-N-benzoyl-3-methyl-N'-(2-cyano-acetyl)piperazine (190 mg) and 2-chlorobenzothiazole (100 mg) in THF (10 ml). After the reaction was stirred for 10 hours, 4 ml of solution was separated and quenched with MeOH. After solvents were removed under vaccum, the residue was purified using Shimadzu automated preparative HPLC System to give (R)-N-(benzoyl)-3-methyl-N'-[(benzothiazol-2-yl)-2-cyanoacetyl]-piperazine (15.4 mg).

EXAMPLE 2

(R)-N-(benzoyl)-3-methyl-N'-[(benzothiazol-2-yl)-2-oxoacetyl]-piperazine. To the reaction mixture above, acetic peracid (4 ml, 25% in acetic acid) was added and the resulted mixture was stirred for another 1 hour before being quenched by MeOH. After solvents were removed under vaccum, the residue was purified using Shimadzu automated preparative HPLC System to give (R)-N-(benzoyl)-3-methyl-N'-[(benzothiazol-2-yl)-2-oxoacetyl]-piperazine (7.4 mg).

EXAMPLE 3

(R)-N-(benzoyl)-3-methyl-N'-[2-(benzothiazol-5-yl)-2-oxo-1-cyano-ethyl]piperazine. NaHMDS (1.3 ml, 1M in THF) was added into a solution of N-benzoyl-N'-cyanomethylpiperazine (100 mg) and ethyl 5-benzothiazoate (106 mg) in THF (10 ml). The reaction was stirred for 10 hours. After solvents were removed under vaccum, the residue was purified using Shimadzu automated preparative HPLC System to give (R)-N-(benzoyl)-3-methyl-N'-[2-(benzothiazol-5-yl)-2-oxo-1-cyano-ethyl]-piperazine.

EXAMPLE 4

(R)-N-(benzoyl)-3-methyl-N'-[(benzothiazol-5-yl)-2-oxoacetyl]piperazine. NaHMDS (1.3 ml, 1M in THF) was added into a solution of N-benzyl-N'-cyanomethylpiperazine (100 mg) and ethyl 5-benzothiazoate (106 mg) in THF (10 ml). After the reaction was stirred for 10 hours, mCPBA (200 mg, >77%) was added and the resulted mixture was stirred for another 10 hours. Then solvents were removed under vaccum, the residue was purified using Shimadzu automated preparative HPLC System to give compound B-3, (R)-N-(benzoyl)-3-methyl-N'-[(benzothiazol-5-yl)-2-oxoacetyl]-piperazine (1.3 mg).

EXAMPLE 5

(R)-N-(benzoyl)-3-methyl-N'-[2-(5-methoxy-benzothiazol-2-yl)-2-imino-1-cyano-ethyl]-piperazine. NaHMDS (0.77 ml, 1M in THF) was added into a solution of (R)-N-benzyl-3-methyl-N'-cyanomethylpiperazine (100 mg) and 2-cyano-5-methoxy-benzothiazole (58 mg) in THF (10 ml). The reaction was stirred for 10 hours. Then 4 ml of the reaction mixture was separated and quenched with MeOH. After solvents were removed under vaccum, the residue was purified using Shimadzu automated preparative HPLC System to give (R)-N-(benzoyl)-3-methyl-N'-[2-(5-methoxy-benzothiazol-2-yl)-2-imino-1-cyano-ethyl]-piperazine (1.3 mg).

EXAMPLE 6

(R)-N-(benzoyl)-3-methyl-N'-[(5-methoxy-benzothiazol-2-yl)-2-oxoacetyl]-piperazine. The reaction mixture above was left stirring open to air for another 10 hours before being quenched by MeOH. After solvents were removed under vaccum, the residue was purified using Shimadzu automated preparative HPLC System to give (R)-N-(benzoyl)-3-methyl-N'-[(5-methoxy-benzothiazol-2-yl)-2-oxoacetyl]-piperazine (2.3 mg).

Table 3 lists further examples made using the reactions described above.

TABLE 3

| Example | Structure | MS (M + H)+ Calcd | MS(M + H)+ Observ. And Retention Time |
|---|---|---|---|
| 1 | benzothiazole-CH(CN)-C(=O)-N(piperazine with methyl)-C(=O)-phenyl | 405.14 | 405.09 Rf = 1.75 min. (column E) |

TABLE 3-continued

| Example | Structure | MS (M + H)+ Calcd | MS(M + H)+ Observ. And Retention Time |
|---|---|---|---|
| 2 | 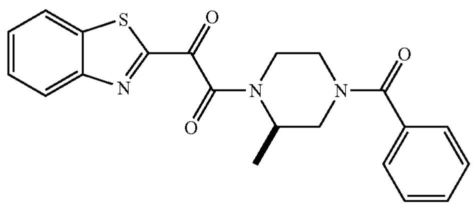 | 394.12 | 394.12<br>Rf = 1.62 min.<br>(column E) |
| 3 | 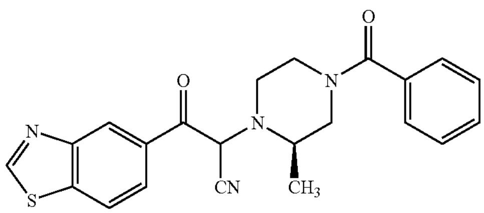 | 405.14 | 405.11<br>Rf = 1.63 min.<br>(column L) |
| 4 | 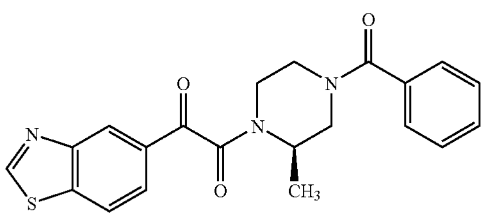 | 394.12 | 394.28<br>Rf = 1.31 min.<br>(column C) |
| 5 | 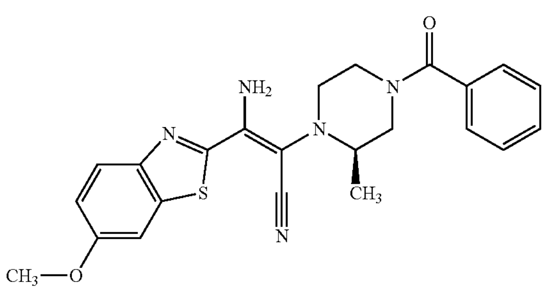 | 434.17 | 434.12<br>Rf = 1.94 min.<br>(column H) |
| 6 | 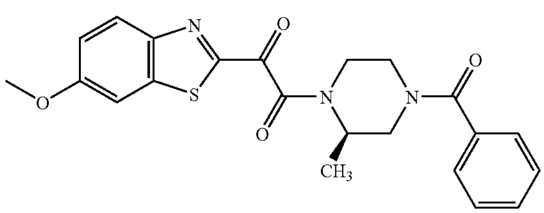 | 424.13 | 424.15<br>Rf = 1.56 min.<br>(column C) |
| 7 | 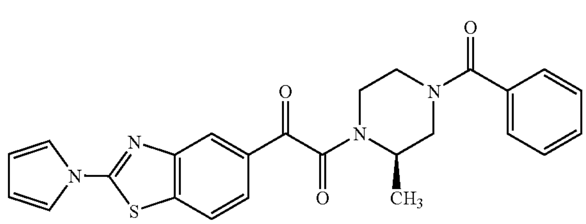 | 459.15 | 459.25<br>Rf = 1.75 min.<br>(column C) |

TABLE 3-continued

| Example | Structure | MS (M + H)+ Calcd | MS(M + H)+ Observ. And Retention Time |
|---|---|---|---|
| 8 | 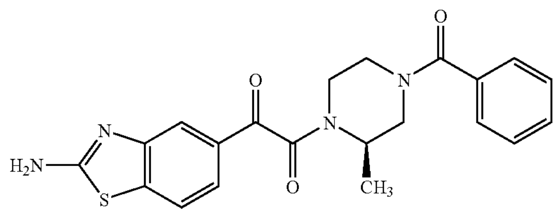 | 409.13 | 409.23 Rf = 1.12 min. (column C) |
| 9 | 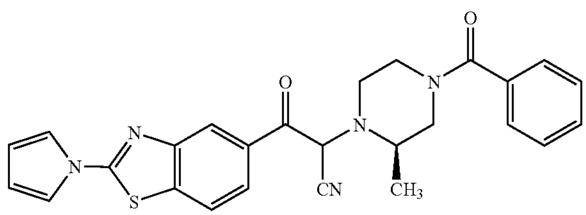 | 470.17 | 470.17 Rf = 2.05 min. (column L) |
| 10 | 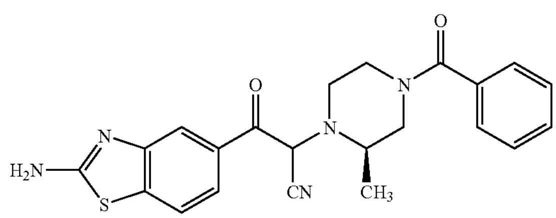 | 420.15 | 420.13 Rf = 1.37 min. (column L) |

The invention claimed is:

1. A compound of Formula I

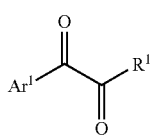

I wherein:
R¹ is

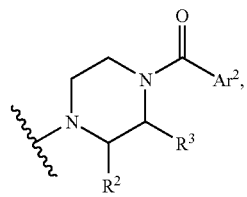

R² and R³ are independently hydrogen or $C_{1-6}$alkyl;

R⁴ and R⁵ are independently hydrogen, halo, cyano, $C_{1-6}$alkoxy, $CO_2R^2$, $CON(R^2)(R^2)$, or Ar⁵;

R⁶ is hydrogen, amino, $C_{1-6}$alkylamino, $C_{1-6}$dialkylamino, or pyrrolyl;

Ar¹ is

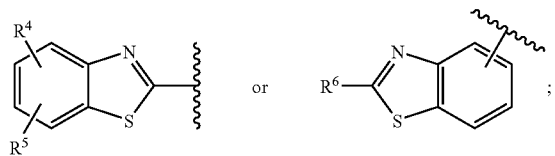

Ar² is phenyl, furanyl, thienyl, or pyrrolyl and is substituted with 0–2 substituents selected from the group consisting of $C_{1-6}$alkoxy, halo, trifluoromethyl, cyano, amino, and hydroxy; and Ar⁵ is pyridinyl, pyrimidinyl, pyrazolyl, triazolyl, or tetraolyl, and is substituted with 0–1 $C_{1-6}$alkyl;

or a pharmaceutically acceptable salt thereof.

2. A compound of claim 1 where $Ar^1$ is

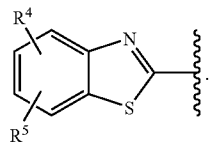

3. A compound of claim 2 where $Ar^1$ is

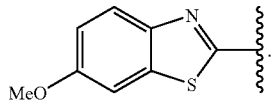

4. A compound of claim 1 where $Ar^1$ is

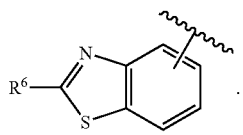

5. A compound of claim 4 where $R^6$ is hydrogen, amino, or pyrrolyl.

6. A compound of claim 1 where $R^2$ and $R^3$ are hydrogen.

7. A compound of claim 1 where $R^2$ is methyl and $R^3$ is hydrogen.

8. A compound of claim 1 where $R^2$ is hydrogen and $R^3$ is methyl.

9. A compound of claim 1 where $Ar^2$ is phenyl and is substituted with 0–2 substituents selected from the group consisting of $C_{1-6}$alkoxy, halo, trifluoromethyl, cyano, amino, and hydroxy.

10. A compound of claim 9 where $Ar^2$ is phenyl.

11. A compound of claim 1 selected from the group consisting of
   (2R)-1-[2-(2-benzothiazolyl)-1,2-dioxoethyl]-4-benzoyl-2-methyl-piperazine;
   (2R)-4-benzoyl-1-[2-(6-methoxy-2-benzothiazolyl)- 1,2-dioxoethyl]-2-methyl-piperazine;
   (2R)-1-[2-(5-benzothiazolyl)-1,2-dioxoethyl]-4-benzoyl-2-methyl-piperazine;
   (2R)-4-benzoyl- 1-[1,2-dioxo-2-[2-(1H-pyrrol-1-yl)-5-benzothiazolyl]ethyl]-2-methyl-piperazine; and
   (2R)- 1 -[2-(2-amino-5 -bezothiazolyl)- 1,2-dioxoethyl]-4-benzoyl-2-methyl-piperazine;
   or a pharmaceutically acceptable salt thereof.

12. A compound of Formula IIa or IIb

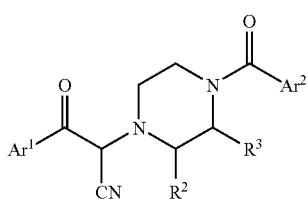

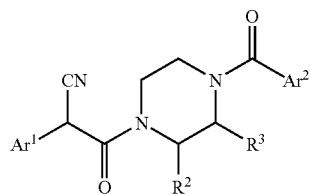

wherein:
   $Ar^1$ is

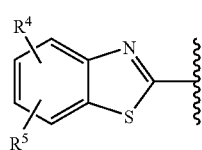 or 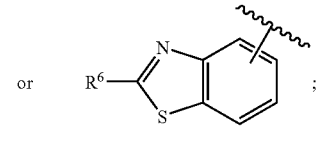;

$Ar^2$ is phenyl, furanyl, thienyl, or pyrrolyl and is substituted with 0–2 substituents selected from the group consisting of $C_{6-4}$alkoxy, halo, trifluoromethyl, cyano, amino, and hydroxy;
   $R^2$ and $R^3$ are independently hydrogen or $C_{1-6}$alkyl;
   $R^4$ and $R^5$ are independently hydrogen, halo, or $C_{1-6}$alkoxy; and
   $R^6$ is hydrogen, amino, $C_{1-6}$alkylamino, $C_{1-6}$dialkylamino, or pyrrolyl;
   or a pharmaceutically acceptable salt thereof.

13. A pharmaceutical composition comprising a therapeutically effective amount of a compound of claim 1 and a pharmaceutically acceptable carrier.

14. A pharmaceutical composition comprising a therapeutically effective amount of a compound of claim 12 and a pharmaceutically acceptable carrier.

15. A method of treating HIV infection in a patient comprising administering a therapeutically effective amount of a compound of claim 1.

16. The method of claim 15 further comprising administering a therapeutically effective amount of at least one other agent for treating HIV selected from the group consisting of HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

17. A method of treating HIV infection in a patient comprising administering a therapeutically effective amount of a compound of claim 12.

18. The method of claim 17 further comprising administering a therapeutically effective amount of at least one other agent for treating HIV selected from the group consisting of HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

* * * * *